(12) United States Patent  (10) Patent No.: US 7,768,263 B2
Nagao et al.  (45) Date of Patent: Aug. 3, 2010

(54) MAGNETIC RESONANCE IMAGING APPARATUS AND METHOD

(75) Inventors: Hisako Nagao, Chiba (JP); Takayuki Abe, Chiba (JP); Tetsuhiko Takahashi, Saitama (JP); Masahiro Takizawa, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 42 days.

(21) Appl. No.: 12/331,005

(22) Filed: Dec. 9, 2008

(65) Prior Publication Data

US 2009/0091323 A1 Apr. 9, 2009

Related U.S. Application Data

(63) Continuation of application No. 11/662,108, filed on Mar. 6, 2007, now Pat. No. 7,486,076.

(51) Int. Cl.
*G01V 3/00* (2006.01)

(52) U.S. Cl. ........................ 324/307; 324/309

(58) Field of Classification Search ......... 324/300–322; 600/407–445
See application file for complete search history.

(56) References Cited

U.S. PATENT DOCUMENTS

| 5,323,111 A | 6/1994 | Katsunori |
| 5,551,430 A | 9/1996 | Blakeley et al. |

(Continued)

FOREIGN PATENT DOCUMENTS

| JP | 5-269113 | 10/1993 |

(Continued)

OTHER PUBLICATIONS

Kruger, David G., et al., "Continuously moving table data acquisition method for long FOV contrast-enhanced MRA and whole-body MRI", *Magnetic Resonance in Medicine*, vol. 47, Issue 2, pp. 224-231, Jan. 23, 2002.

(Continued)

*Primary Examiner*—Brij B Shrivastav
(74) *Attorney, Agent, or Firm*—Cooper & Dunham LLP (57) ABSTRACT

A magnetic resonance imaging apparatus comprises static magnetic field generating means for generating a static magnetic field in an imaging space, a gradient magnetic field generating means for generating a gradient magnetic field in the imaging space, high-frequency magnetic field generating means for generating a high-frequency magnetic field so as to induce nuclear magnetic resonance in a subject placed in the imaging space, signal receiving means for detecting a nuclear magnetic resonance signal from the subject, signal processing means for reconstructing an image by using the detected nuclear magnetic resonance signal, display means for displaying the image, a table for placing the subject thereon to dispose the subject in the imaging means, and table moving means for moving the table on which the subject is placed.

While moving the portions to be imaged of the subject continuously or stepwise in the imaging space and disposing the subject, a whole-body image of a large region of the subject is created.

The magnetic resonance imaging apparatus further comprises means for detecting information on the displacement of the subject from a desired position and setting means for setting movement information on the table according to the displacement information.

The table moving means moves the table according to the movement information set by the setting means to capture the whole-body image.

12 Claims, 11 Drawing Sheets

(a)

(b)

U.S. PATENT DOCUMENTS

| | | | |
|---|---|---|---|
| 5,877,732 A * | 3/1999 | Ziarati | 345/8 |
| 5,928,148 A | 7/1999 | Wang et al. | |
| 6,045,262 A | 4/2000 | Igeta et al. | |
| 6,794,869 B2 * | 9/2004 | Brittain | 324/309 |
| 6,801,034 B2 * | 10/2004 | Brittain et al. | 324/309 |
| 6,822,447 B1 | 11/2004 | Yamagata | |
| 6,870,367 B2 * | 3/2005 | Kirsch | 324/309 |
| 6,946,836 B2 | 9/2005 | Kuhara | |
| 7,030,615 B2 | 4/2006 | Gortler | |
| 7,034,535 B2 | 4/2006 | Yamagata | |
| 7,180,074 B1 * | 2/2007 | Crosetto | 250/370.09 |
| 7,319,325 B2 | 1/2008 | Petot et al. | |
| 7,511,489 B2 * | 3/2009 | Fautz et al. | 324/307 |
| 7,535,226 B2 * | 5/2009 | Takahashi et al. | 324/309 |
| 2002/0140423 A1 | 10/2002 | Brittain | |
| 2002/0143247 A1 | 10/2002 | Brittain et al. | |
| 2007/0038069 A1 * | 2/2007 | Itagaki et al. | 600/410 |
| 2007/0145977 A1 | 6/2007 | Keupp et al. | |
| 2007/0222442 A1 | 9/2007 | Aldefeld et al. | |
| 2008/0071166 A1 * | 3/2008 | Miyazaki | 600/419 |
| 2009/0177076 A1 * | 7/2009 | Aldefeld et al. | 600/410 |
| 2009/0177078 A1 * | 7/2009 | Takizawa et al. | 600/415 |
| 2009/0264735 A1 * | 10/2009 | Steckner | 600/422 |

FOREIGN PATENT DOCUMENTS

| | | |
|---|---|---|
| JP | 2000-107151 | 4/2000 |
| JP | 2001-95773 | 4/2001 |
| JP | 2003-135429 | 5/2003 |
| JP | 2003-204952 | 7/2003 |
| JP | 2004-57237 | 2/2004 |
| JP | 2004-236849 | 8/2004 |
| WO | WO03/041577 A1 | 5/2003 |

OTHER PUBLICATIONS

Riederer, Stephen J., et al., "Long Field-of-View MRI Using Continuous Table Motion", pp. 81-86.

Zhu, Yudong, "Extended-FOV Magnetic Resonance Imaging With Table Trasalation And Frequency Cycling", *IEEE*, pp. 955-958, 2002.

Sep. 29, 2008 official action in connection with a counterpart Japanese patent application No. 2008-212310.

English translation of May 23, 2008 Chinese official action in connection with counterpart Chinese Patent application No. 20050028869.6.

Nov. 10, 2009 European Search Report in connection with a counterpart European Application No. 05 78 1380.

* cited by examiner

MAGNETIC RESONANCE IMAGING APPARATUS AND METHOD

CROSS-REFERENCE TO RELATED APPLICATION

This application is a Rule 1.53(b) Continuation of U.S. Ser. No. 11/662,108, filed Mar. 6, 2007 now U.S. Pat. No. 7,486,076, the entire contents of which are incorporated herein by reference.

TECHNICAL FIELD

The present invention relates to a magnetic resonance imaging (hereinafter referred to as MRI) apparatus and method, particularly to an MRI apparatus and method for imaging a wide range or a whole-body of a subject while moving the table capable of making accurate positioning of the respective regions for imaging

BACKGROUND ART

MRI apparatus is for obtaining a magnetic resonance image to represents physical characteristics of a subject (hereinafter referred to as an MR image), when electromagnetic waves are irradiated to a subject placed in a homogeneous static magnetic field, by detecting nuclear magnetic resonance signals (hereinafter referred to as NMR signals) from the subject using NMR phenomenon being generated in nuclei of atomic elements forming the body of the subject, and reconstructing an image using the detected NMR signals.

In MRI, a technique for imaging a wide range or an entire body region of a subject while moving the table on which the subject is placed in a gantry of an MRI apparatus is well known. There are two ways of moving the table in such technique. One is a method that divides a wide range or the entire body region of a subject into a plurality of blocks and to construct an image, while moving the table, stepwise in each block (for example, see Patent Document 1). Another one is a method to construct an image of a wide range or the entire body region of a subject by imaging and moving the table continuously at the same time (for example, see Patent Document 2 or Non-Patent Document 1).

Patent Document 1: U.S. Pat. No. 6,311,085
Patent Document 2: JP-A-2004-661
Non-Patent Document 1: Kruger D G, Riederer S J, Grimm R C, Rossman P J.: Continuously Moving Table Data Acquisition Method for Long FOV Contrast-Enhanced MRA and Whole-body MRI. Magnetic Resonance in Medicine 47(2): 224-231 (2002).

However, moving direction of the table with regard to the above-mentioned two methods is only toward central-axis of longitudinal direction of the table. Also, in the method for segmenting a wide range or the entire body range of the subject into a plurality of blocks and moving the table stepwise in each block, the field of view (hereinafter referred to as FOV) to be set in each block is constant, and they are generally arranged at even intervals only in the central-axis direction of longitudinal direction of the table.

DISCLOSURE OF THE INVENTION

Problems to be Solved

However, the inventors of the present invention have discovered the problems listed below as a result of examining the above-mentioned conventional techniques.

For example, in the case of imaging a subject, while moving the table, either by blocks or continuously along the center of the body axis of the subject using the above-mentioned conventional technique and the central axis of longitudinal direction of the table is set so that it passes through the center of the static magnetic field of the MRI apparatus, when the subject is placed being tilted toward the central axis of the longitudinal direction of the table the central body axis of the subject does not always pass through the center of static magnetic field which leads to the subject running off the FOV.

The objective of the present invention is to provide an MRI apparatus and method capable of properly setting the imaging position of the respective regions of a subject in the MRI for imaging a wide range or the entire body range of the subject while in motion on the table.

In order to achieve the above-mentioned objective, an MRI apparatus of the present invention for constructing a whole-body image of a subject while moving the respective imaging regions of the subject in the imaging space continuously or stepwise comprises:

static magnetic field generating means for generating a static magnetic field in an imaging space;

gradient magnetic field generating means for generating a gradient magnetic field in the imaging space;

high-frequency magnetic field generating means for generating high-frequency magnetic field so as to induce nuclear magnetic resonance in the subject placed in the imaging space;

signal receiving means for detecting a nuclear magnetic resonance signal from the subject;

signal processing means for reconstructing an image using the detected nuclear magnetic resonance signal;

display means for displaying the image;

a table for placing the subject thereon to dispose the subject in the imaging space; and table moving means for moving the table on which the subject is placed, characterized in a magnetic resonance imaging apparatus for obtaining the whole-body image of the subject while moving the respective imaging regions of the subject continuously or stepwise in the imaging space comprising:

means for detecting information on the displacement of the subject from a desired position; and setting means for setting information for moving the table according to the displacement information, wherein the table moving means moves the table based on the information for moving the table set by the setting means to obtain the whole-body image.

The above-mentioned objective can be achieved also by an MRI method, and the MRI method of the present invention is for obtaining the whole-body image of the subject by moving the respective imaging regions of the subject continuously or stepwise in an imaging space, including:

(1) a step for setting information for movement of the table on which the subject is placed taking into consideration displacement in the case that the subject is displaced from the desired position; and (2) a step for creating the whole-body image by moving the table based on the proceeding of the movement being set by the step (1).

In accordance with the present invention, it is possible to provide an MRI apparatus and method capable of properly setting the imaging position of the respective regions of the subject in the case of imaging a wide range or the entire body range of the subject by moving the table.

BRIEF DESCRIPTION OF THE DIAGRAMS

BEST MODE FOR CARRYING OUT THE INVENTION

Hereinafter, preferable embodiments of the MRI apparatus of the present invention will be described in detail referring to the attached diagrams.

In all of the diagrams for illustrating embodiments of the present invention, those having the same function are encoded the same and the repeated description thereof will be omitted.

Figure 1:
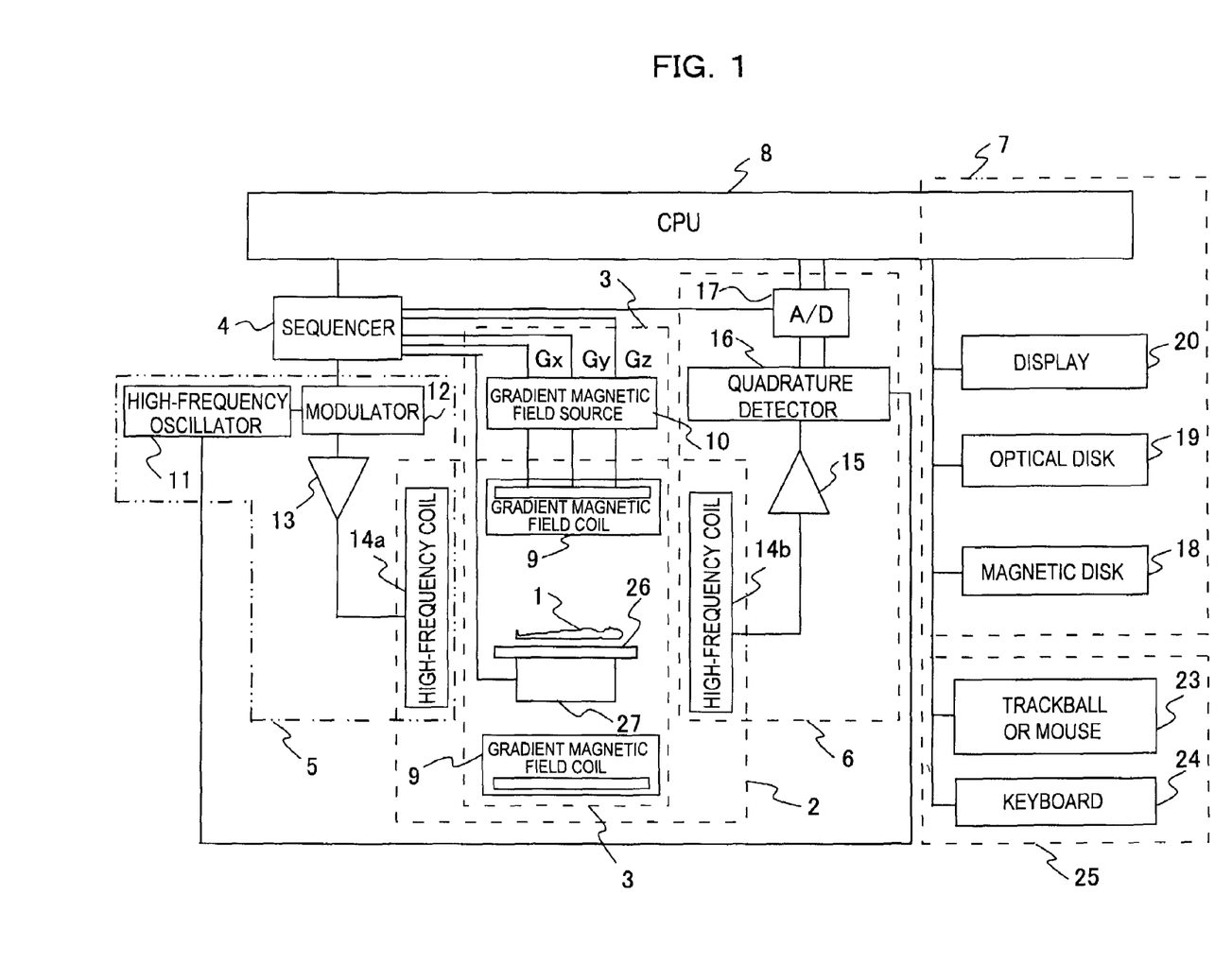
FIG. 1 is a block diagram showing the general configuration relating to one embodiment of an MRI apparatus to which the present invention is applied.

First, an outline of the MRI apparatus of the present invention will be described based on FIG. 1. FIG. 1 is a block diagram showing a general configuration relating to one embodiment of MRI apparatus to which the present invention is applied. This MRI apparatus is for obtaining a tomographic image of a subject using a nuclear magnetic resonance (NMR) phenomenon, comprising static magnetic field generating system 2, gradient magnetic field generating system 3, transmission system 5, reception system 6, signal processing system 7, sequencer 4 and central processing unit (CPU) 8 as shown in FIG. 1.

Static magnetic field generating system 2 is, used with the vertical magnetic field method, for generating a homogeneous static magnetic field to the imaging space of subject 1 in the direction orthogonal to the body axis of the subject, and a static magnetic field source using permanent magnet method, normal conducting magnet method or super-conducting magnetic method is placed around subject 1.

Gradient magnetic field generating system 3 is formed by gradient magnetic field coil 9 being coiled to generate gradient magnetic field in 3 axis-directions of X, Y and Z being coordination system (coordination system at rest) of MRI apparatus and gradient magnetic field source 10 for driving the respective gradient magnetic field coils, and is for generating gradient magnetic fields Gx, Gy and Gz in 3 axis directions X, Y and z according to the command from sequencer 4 which will be described later. Upon imaging, a slice section with respect to subject 1 is set by applying a gradient magnetic field pulse in slice direction (Gs) being selected in the direction orthogonal to the slice cross-section (imaging cross-section), a gradient magnetic field pulse in phasing encode direction (Gp) and a gradient magnetic field pulse in frequency encode direction (Gf) being allotted to two remained directions that are orthogonal to the slice cross-section and are orthogonal to each other are applied, and positional information of the respective directions is encoded.

Sequencer 4 is control means to repeatedly apply a high-frequency magnetic field pulse (hereinafter referred to as "RF pulse") and gradient magnetic field pulse at a predetermined pulse sequence, is operated under control of CPU 8, and is for transmitting various necessary commands necessary for data collection of tomograms of subject 1 to transmission system 5, gradient magnetic field generating system 3 and reception system 6.

Transmission system 5 is for irradiating RF pulses to generate nuclear magnetic resonance to atomic nucleus spin of atomic elements that are forming body tissues of subject 1, comprising high-frequency oscillator 11, modulator 12, high-frequency amplifier 13 and high-frequency coil (transmission coil or RF irradiation coil) 14a on the transmission side. The RF pulse is irradiated to subject 1 as follows: a high-frequency pulse outputted from high-frequency oscillator 11 is amplitude-modulated by modulator 12 at the timing commanded from sequencer 4, and provided to high-frequency coil 14a which is placed in the vicinity of subject 1 after the modulated high-frequency pulse is amplified by high-frequency amplifier 13.

Reception system 6 is for detecting echo signals (NMR signals) being discharged by nuclear magnetic resonance of atomic nucleus spin forming body tissues of subject 1, comprising high-frequency coil (reception coil) 14b on the reception side, signal amplifier 15, quadrature detector 16 and A/D converter 17. NMR signals responsive to subject 1 being induced by electromagnetic waves irradiated from high-frequency coil 14a on the transmission side are detected by high-frequency coil 14b placed in the vicinity of subject 1, amplified by signal amplifier 15, segmented by quadrature detector 16 into two lines of signals that are orthogonal to each other, each of them converted into digital quantity by A/D converter and transmitted to signal processing system 7.

Signal processing system 7 is for executing various data-processing, and processing such as display and storage of the processing result, comprising external storage device such as optical disk 19 and magnetic disk 18 and display 20 formed by devices such as CRT. When data from reception system 6 is inputted to CPU 8, CPU 8 executes processes such as signal processing and imaging reconstruction, displays tomograms of subject 1 which is the result of the processing, and records them in devices such as magnetic disk 18 of the external storage device.

Operation unit 25 is for inputting various control information of MRI apparatus or control information on processing being executed in the above-mentioned signal processing system 7, comprising trackball or mouse 23 and keyboard 24. The operation unit 25 is placed in the vicinity of display 20, wherein an operator interactively controls various processing of MRI apparatus through operation unit 25 while observing display 20.

Subject 1 is placed on table 26 and transferred to a static magnetic field space. The table 26 is drive-controlled by table-driving unit 27 according to the control command transmitted from sequencer 4. Table-driving unit 27 in the present invention is capable of moving table 26 not only in longitudinal or vertical direction, but also in horizontal direction orthogonal to the longitudinal direction.

In FIG. 1, high-frequency coil 14a on the transmission side and gradient magnetic field coil 9 are placed around the space where subject 1 is placed. Also, high-frequency coil 14b on the reception side is placed either facing or surrounding subject 1.

Currently the imaging target nuclide of MRI apparatus being clinically prevalent is hydrogen nucleus (proton) that is a main component of the subject. Through imaging the information relating to the spatial distribution of proton density or special distribution of relaxation time in excitation state, the imaging of figure or function of regions such as head, abdomen or limbs of a human body is performed two-dimensionally or three-dimensionally.

EMBODIMENT 1

Figure 2:
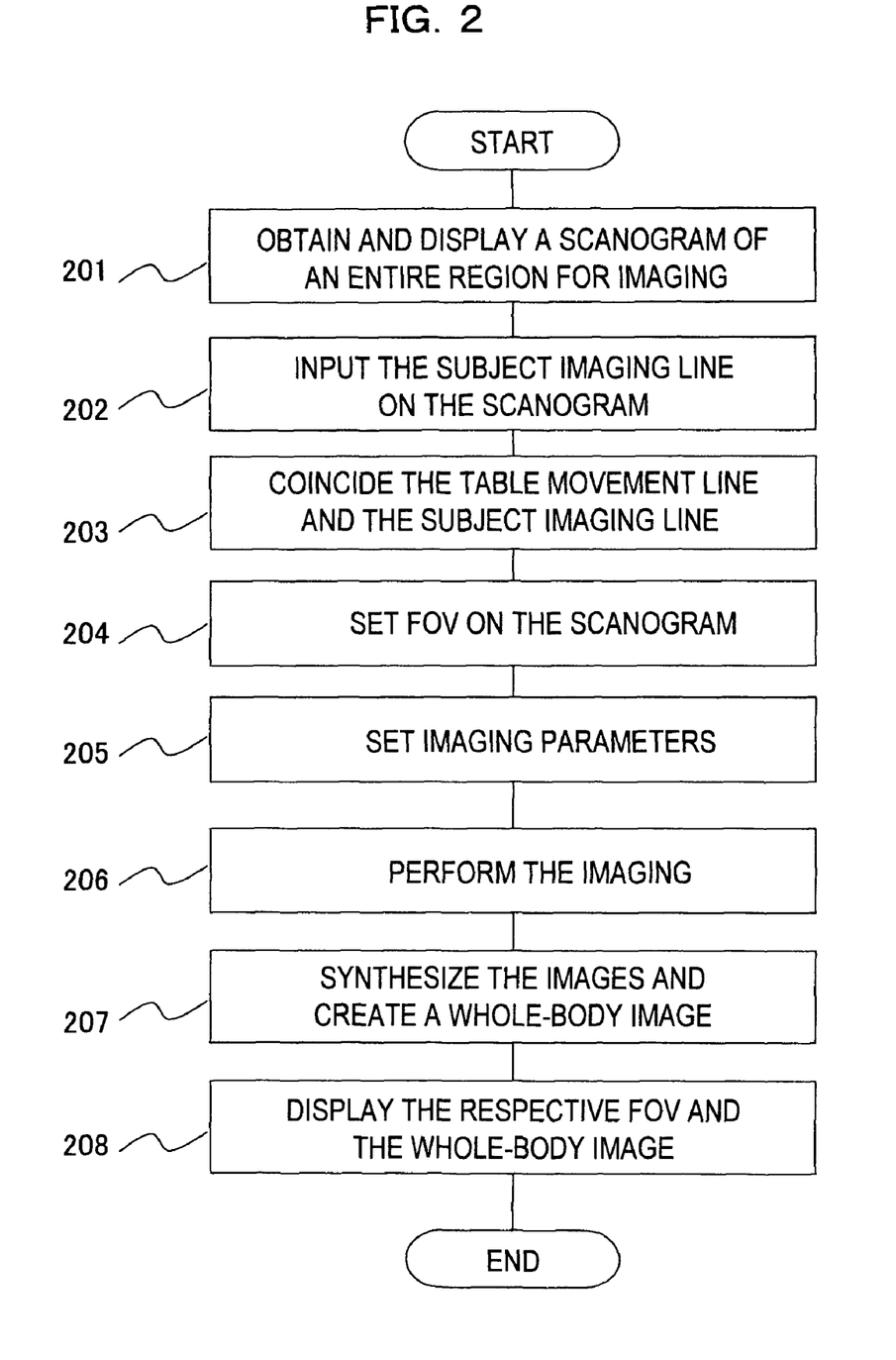
FIG. 2 is a flow chart showing a procedure outline of the MRI in embodiment 1.

The MRI apparatus and method relating to embodiment 1 of the present invention will be described using FIGS. 2~7. First, FIG. 2 is a flow chart showing the procedure outline of the MRI in embodiment 1. Each step of FIG. 2 will be described in order. Embodiment 1 is an embodiment of imaging by segmenting the region of a wide range or an entire range of the body of a subject into a plurality of blocks and moving the table in parallel by the blocks while keeping the table in the same direction.

(Step 201)

Figure 3:
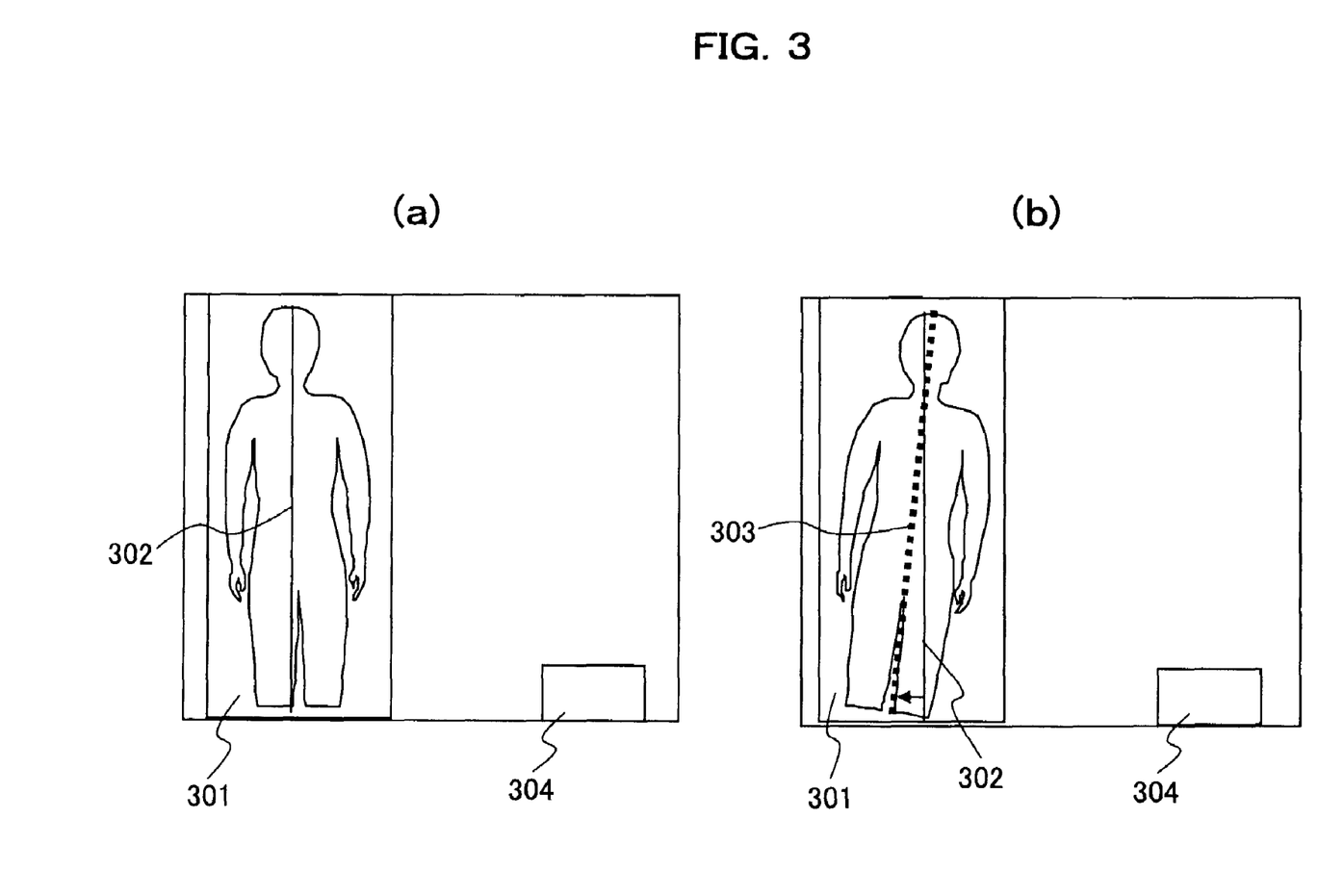
FIG. 3 is a diagram representing a scanogram being shown on a display, (a) is a case that the initial position of the movement line of the table coincides with the central body axis of a subject, and (b) is a case that they do not coincide with each other.

As a preparation for the present imaging, a scanogram of the entire region of the imaging target of the subject is imaged and displayed on display 20. Scanogram is a simple image for setting a position of the imaging region, and generally is imaged using pulse sequence that has low resolution and high speed (for example, see JP-A-1993-253208 as a conventional technique relating to the scanogram). FIG. 3 is a scanogram displayed on display 20 in the present embodiment, FIG. 3 (a) is a case that the central axis of longitudinal direction of the table being placed where the central axis of longitudinal direction of the table coincides with the central axis direction of the imaging space (hereinafter referred to as initial position of the table movement line) coincides with the central axis of the subject, and FIG. 3 (b) is a case that the initial position of the table movement line does not coincide with the central axis of the subject. In FIG. 3, 301 represents a scanogram, 302 is a line indicating the initial position of the table movement line, a dotted line shown in 303 is a line indicating the central axis of the subject and 304 is a start button for inputting information such as starting message indicating the starting of imaging. According to FIG. 3, the initial position of the table movement line coincides with the central axis of the subject in the case of FIG. 3 (a) since the subject is placed straight in the center of the table, but since the subject is placed being tilted in the case of FIG. 3 (b) the initial position of the table movement line and the central axis of the subject do not coincide with each other.

(Step 202)

The subject imaging line (a line necessary for guiding the movement in the present imaging) is inputted on the scanogram. In the case of FIG. 3 (a), the present step will be omitted since the initial position of the table movement line coincides with the central axis of the subject, and the next step is to proceed or the initial position of the table movement line is set as the subject imaging line. On the other hand, in the case of FIG. 3 (b), the subject imaging line is inputted on a scanogram displayed on display 20. To be more precise, the subject imaging line is plotted on the central axis of the subject using trackball or mouse 23, or keyboard 24. For example, in the case of using a straight line for plotting the subject imaging line, it is plotted by assigning a start point and an end point of the line on a screen of display 20. Also, in the case of using a curve for plotting the subject imaging line, it can be plotted by assigning a plurality of points passing through the curve and obtaining the curve to pass through those points by interpolation.

(Step 203)

Upon executing imaging in step 206 as mentioned below, the table movement line is adjusted for the table to be moved so that the region of the subject corresponding to the subject imaging line inputted in step 202 passes through the center of the static magnetic field (center of the imaging space) of the MRI apparatus. In concrete terms, the table movement line is rotated or moved in parallel so that the table movement line coincides with the subject imaging line being inputted in step 202 through the operation using trackball or mouse 23, or keyboard 24. When the initial position of the table movement line and the subject imaging line coincide with each other as in FIG. 3 (a), the present step will be omitted. When the subject imaging line is plotted with a curve, the curve itself is set as the table movement line.

In the present embodiment, the relationship between the coordination system having the center of the static magnetic field of the MRI apparatus as a coordination origin and factors such as the position and distance of setting of the table is recorded in advance in a device such as a magnetic disk, and the position of the scanogram imaged in (step 201) or the position of the line and so forth displayed thereon also can be converted into the coordination system having the center of the static magnetic field of the MRI apparatus as a coordinate origin.

In the present embodiment, the position of the coordinate system (having the central position of static magnet field as a coordinate origin) of an MRI apparatus in the initial position of the table movement line is acquired in advance as design data, and the degree of positional difference between the table movement line set by the present step and the initial position of the table movement line is calculated based on the data on the scanogram. Through the result of the calculation, the degree of the displacement of the subject placed on the table is detected, and it is set so that information for the movement of the table in order for the subject imaging line to pass through the center of the static magnetic field of the MRI apparatus can be calculated in a device such as CPU.

The table movement line being set in the present step is stored temporarily, for example, in the CPU memory.

(Step 204)

Figure 4:
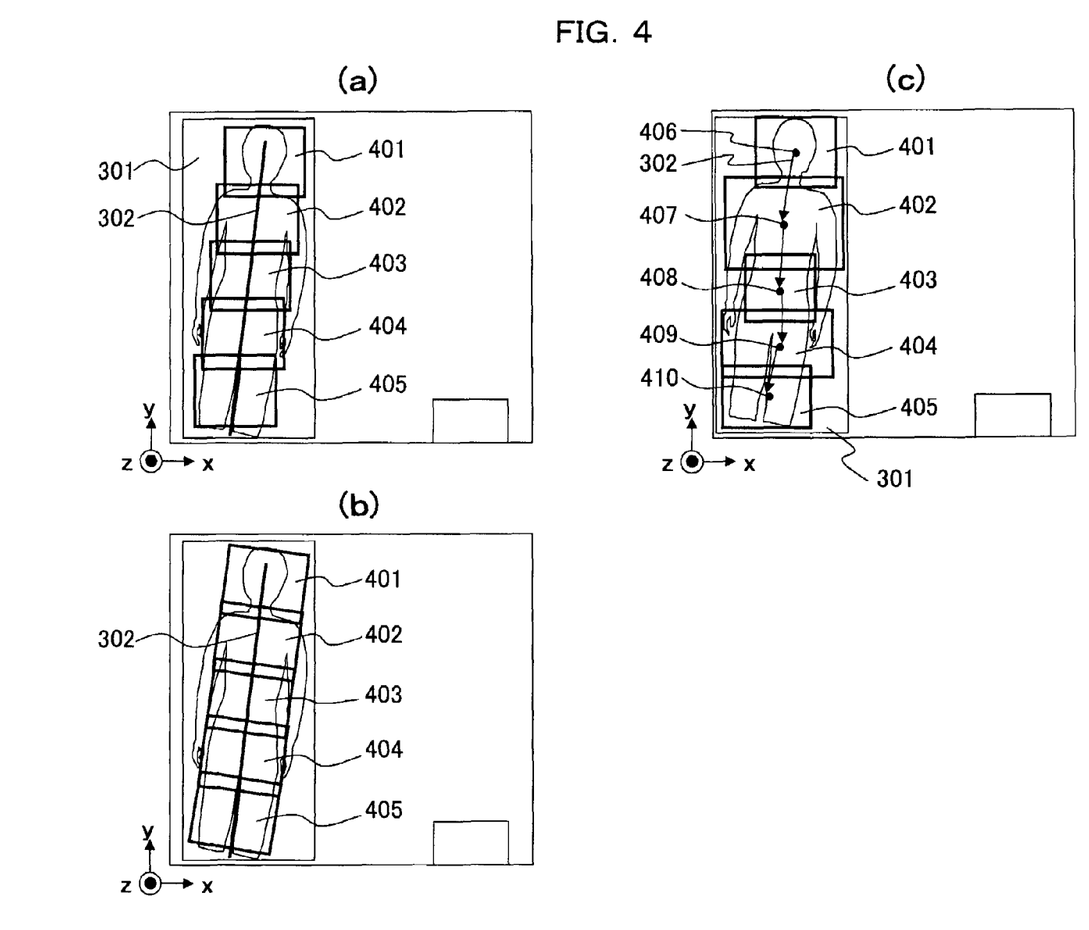
FIG. 4 are diagrams showing an example of setting FOV, (a) is a method for setting one side of the rectangle representing FOV to be parallel to the central axis of longitudinal direction of the table and further setting so that the center of them overlaps with a table movement line, (b) is a method for setting one side of a rectangle representing FOV to be parallel to the table moving line having a gradient to the central axis of longitudinal direction of the table and further setting so that the center of them fall on the table movement line, and (c) is a method for changing the position and size of the respective FOV after FOV has been set as described in methods (a) or (b).

FOV for the imaging executed by segmenting a wide range or an entire body range of a subject into a plurality of blocks is set. An example for setting FOV is shown in FIG. 4. FIG. 4 is a case of setting the rectangles representing FOV 401~405 for imaging a coronal tomogram on the scanogram. In FIG. 4, the case that the number of FOV is five is shown (same in FIGS. 5, 6 and 9 below), and the setting of FOV 401~405 is carried out by interconnecting them by small portions. This setting has the advantage of avoiding having the regions of the subject that are not imaged, as well as being able to easily connect image data between adjacent FOV in the step which will be described later.

There are several setting methods of FOV in the present embodiment, and FIG. 4 (a) is a method for setting one side of the rectangle representing FOV to be parallel to the central axis of longitudinal direction of the table, and further setting the center of them to fall on the movement line of the table. In the present method, there is no need to implement the oblique imaging that is for making gradient magnetic field oblique to be applied. Here, the oblique imaging indicates an imaging method to apply two or more gradient magnetic fields (in X-direction, Y-direction or Z-direction) using a technique such as the one disclosed in JP-A-1995-23931 for the purpose of either frequency encoding or phase encoding.

Next, FIG. 4 (b) is a method for setting one side of the rectangle representing FOV parallel to the table movement line having a gradient to the central axis of longitudinal direction of the table, and further setting the center of them to fall on the table movement line. When FOV is set for imaging accordingly, an oblique imaging is carried out by applying a gradient magnetic field that is made oblique corresponding to the table movement line shown in FIG. 4 (b) having a gradient to Y-axis.

FIG. 4 (c) illustrates a case, after FOV are set in the same manner as FIG. 4 (a) or (b), of changing the position and size of the respective FOV. To change the position or size of FOV, a method such as to drag one of the four corners of the rectangles representing FOV using a mouse, or to provide a window for inputting numbers corresponding the FOV and input the number there to specify the size of FOV using a keyboard can be used. In the case of FIG. 4 (c), the table is moved so that the polygonal lines connecting the center of the respective FOV for the imaging pass through the center of the static magnetic field of the MRI apparatus in the present measurement described below, and the table is stopped for executing the imaging of the respective FOV when the position of the respective black dots (406~410) coincide with the center of the static magnetic field.

It is configured so that the information relating to the FOV setting (factors such as position, size and direction) set by the present step is temporarily stored in, for example, in the CPU memory.

(Step 205)

Using parameters for executing the present imaging, imaging parameters other than FOV setting are inputted. For example, spatial resolution is one of the parameters for imaging. It is desirable in the case of setting FOV that are different in size such as seen in FIG. 4 (c) that each FOV has the same spatial resolution. In the present embodiment, after setting the respective FOV, spatial resolution is adjusted to be the same in the respective FOV for imaging.

Here, spatial resolution can be expressed as follows by formula (1) using the size of FOV and the matrix of one side of an image:

$$Res = FOV/matrix \quad (1)$$

Adjusting the spatial resolution low can provide the effect of shortening the total imaging time, but adjusting it high can provide the effect to be able to diagnose the whole image with image quality of high spatial resolution.

Parameters for imaging such as spatial resolution specified by adjustment in the present step are temporarily stored in, for example, in the CPU memory.

(Step 206)

The present imaging is started by moving the table stepwise by the respective blocks. To be more precise, the table movement line being temporarily stored in the memory in CPU 8 or information relating to the setting for the position and so forth of the respective FOV for imaging or parameters for imaging are sent to sequencer 4, and the present imaging is to be started under control of sequencer 4. In the present imaging, the table is moved as seen in FIG. 1 so that the region of the subject comparable to the table movement line being set on the scanogram passes through the center of static magnetic field of the MRI apparatus. Then the table is moved, and the imaging is performed by the respective blocks when the region of the subject corresponding to the central position of the respective FOV coincides with the central position of the static magnetic field source of the MRI apparatus.

Imaging by step movement of table 26 is executed so that when the imaging of one FOV is finished, the next imaging is executed as soon as the region of the object corresponding to the central position of the next FOV coincides with the central position of the static magnetic field source of the MRI apparatus. The images obtained in the respective FOV are temporarily stored in magnetic disk 18. A concrete example in the case of imaging as moving the table stepwise in the present step will be described later using FIG. 7 (a) and FIG. 7 (b).

(Step 207)

A whole-body image is created by synthesizing images of the respective FOV. The whole-body image is created by reading in the image of the respective FOV temporarily stored in magnetic disk 18 to a memory of CPU 8, and synthesizing the respective images in CPU 8.

Figure 5:
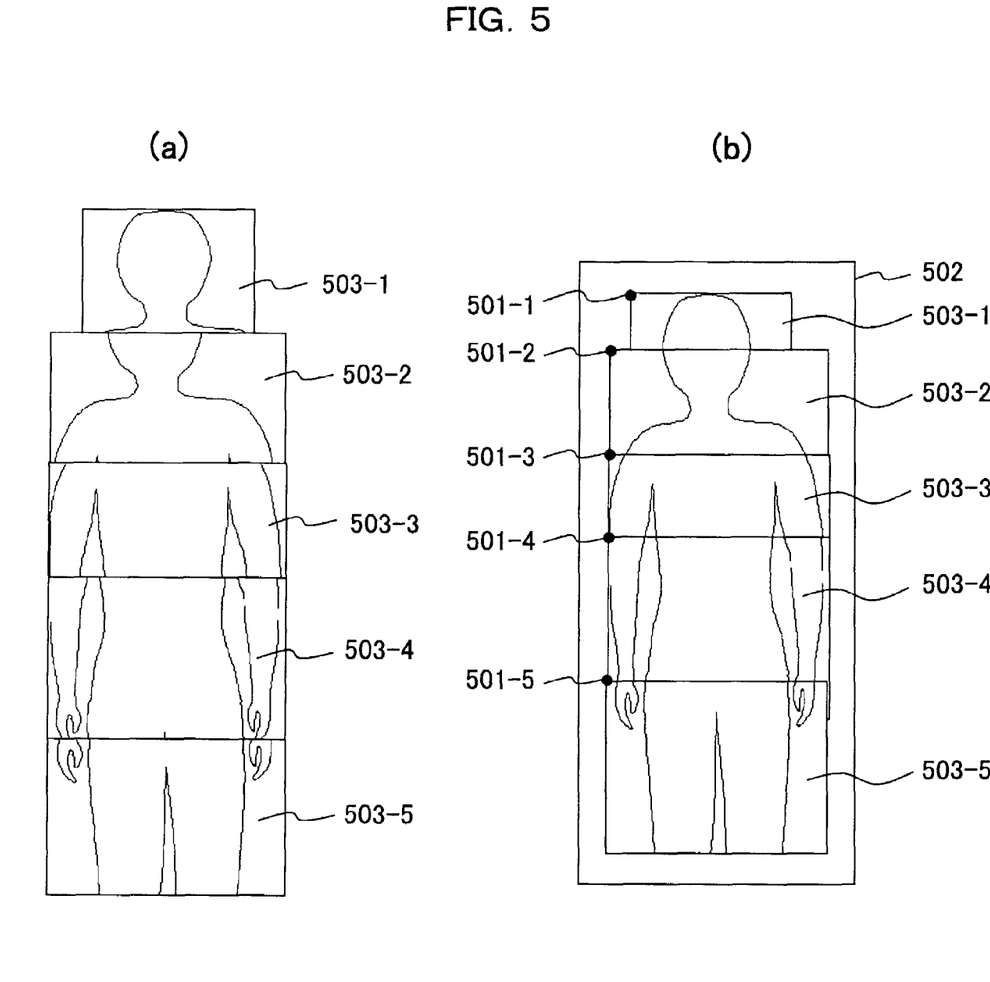
FIG. 5 (a) is a diagram showing an example of the whole-body image wherein the connecting segments of the respective images are discontinuous, and (b) is an example of the whole-body image being created by interlinking the images of FOV together taking into consideration the table movement in the respective steps.

If there is no consideration upon synthesizing on which region of the object is imaged in each image of FOV, the connecting portions turn out to be discontinuous in the whole-body image as seen in FIG. 5 (a). Therefore, the positional relationship of the respective images of FOV upon imaging should be taken into consideration when they are synthesized. More precisely, the whole-body image is created in the large space including the subject by interlinking the images being obtained in the respective FOV while taking into consideration the table movement (X-direction and Y-direction in FIG. 4) in the respective steps. The image created in such manner is shown in FIG. 5 (b). The images in the respective FOV shown in FIG. 5 (b) are imaged based on the reference points (501-1~501-5) shown in the left corner of the respective FOV images. The relative position of the reference points of the respective FOV in an large space including the subject is obtained based on the table moving distance upon shifting the table for imaging the respective images, and the whole-body image is created by interlinking the respective images in the large space including the subject based on these relative positions.

Figure 6:
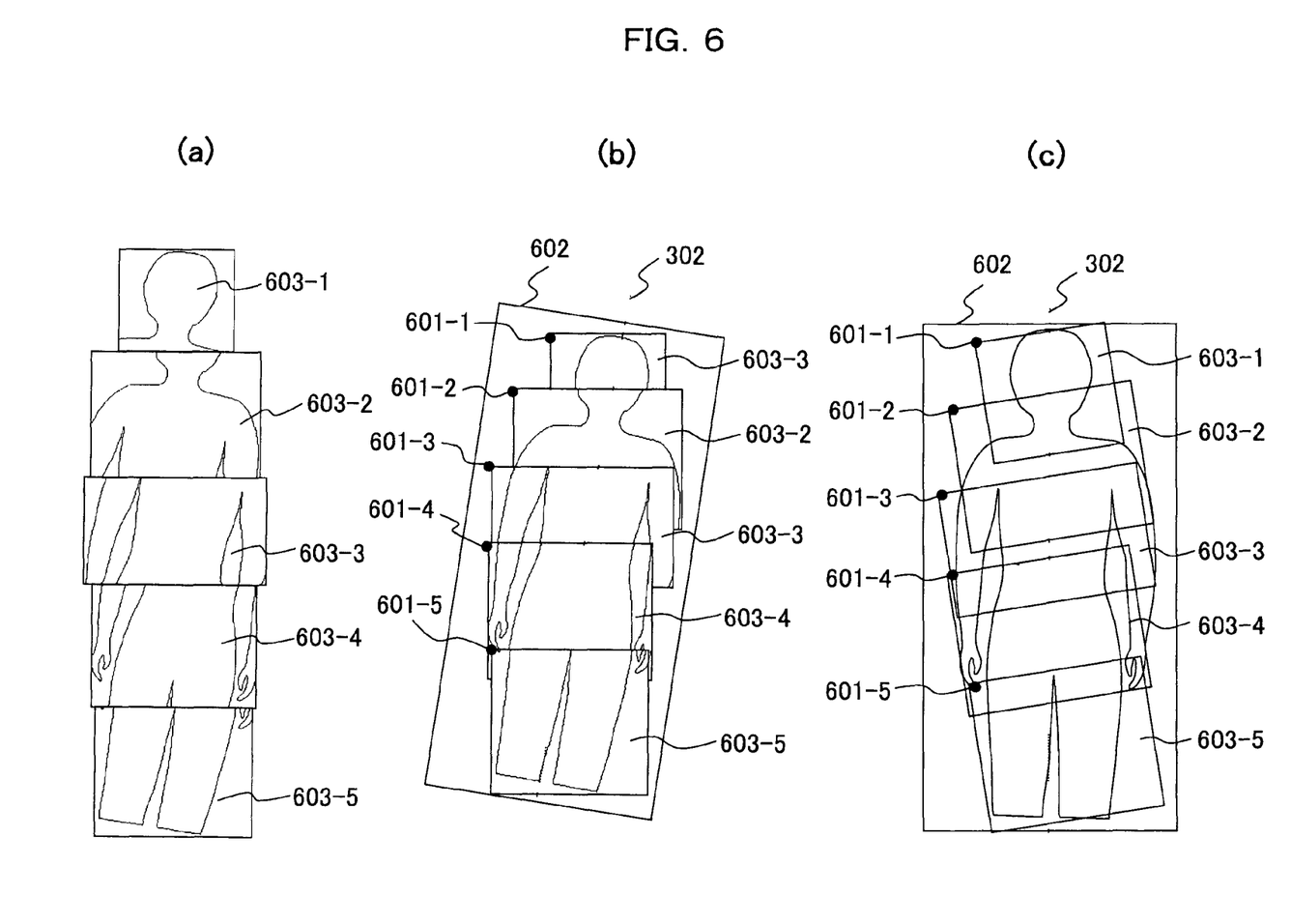
FIG. 6 (a) is a diagram showing an example, when a side of the rectangle representing FOV has a gradient to the central axis of longitudinal direction of the table, of displaying the images of each FOV just as they are in order, (b) is a diagram showing an example of creating a whole-body image in a large space including the subject by interlinking the images obtained in each FOV taking into consideration the table movement in the respective steps and the gradient to longitudinal direction of the table in each FOV upon imaging each FOV, and (c) is a diagram showing an example of displaying (b) so that the table movement line (subject imaging line) should be in an up-and-down direction on a monitor.

The synthesis in the present step of setting FOV so that one side of a rectangle representing FOV to be parallel to the table movement line having a gradient to the central axis of longitudinal direction of the table is implemented in the same manner as in FIG. 5 (b) as seen in the case of step 204 in FIG. 4 (b). FIG. 6 (a) is an example of displaying the images of the respective FOV as they are in order in the case that one side of a rectangle representing FOV has a gradient to the central axis of longitudinal direction of the table, and the connecting portions of these images in the synthesized image turn out to be discontinuous. Thus the whole-body image is created in FIG. 6 (a) in the large space including the subject by interlinking the images obtained in the respective FOV taking into consideration the table movement in the respective steps and the gradient to longitudinal direction of the table in the respective FOV. In FIG. 6 (b), images of the respective FOV are imaged based on the reference points (601-1~601-5) shown in the left corner of the respective FOV images in FIG. 6 (b). The relative position of the reference point of the respective FOV in the large space including the subject, is obtained based on the table moving distance upon shifting the table for imaging the respective images, and the whole-body image is created by interlinking these images taking into consideration the mentioned relative positions and the gradient of the respective FOV to longitudinal direction of the table upon imaging the respective FOV images.

Also, since the body axis of the subject will be displayed on the monitor being tilted in the case such as FIG. 6 (b), the table movement line (subject imaging line) may be set to be the up-and-down direction on the monitor as shown in FIG. 6 (c).

(Step 208)
The images being imaged in the respective FOV and the whole-body image created in step 207 are displayed.

Figure 7:
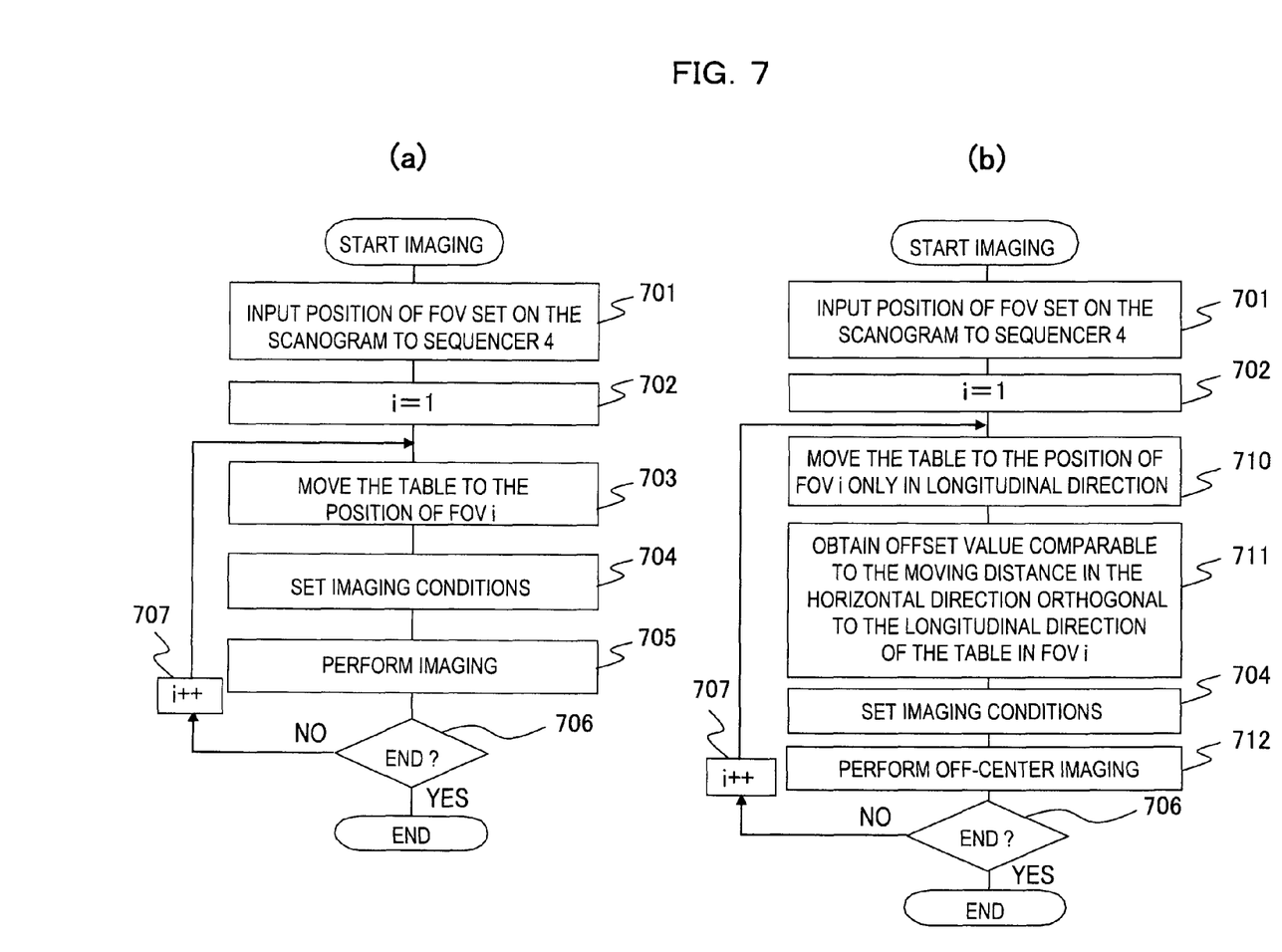
FIG. 7 (a) is a flow chart showing an outline of concrete procedure in the case of carrying out the present imaging while moving the table stepwise in step 206, and (b) is a flow chart showing an example in the case that table 26 is moved only in the longitudinal direction of the table without moving the table in a horizontal direction being orthogonal to the longitudinal direction.

Next, FIG. 7 (a) and FIG. 7 (b) are flow charts showing the concrete procedure outlines in step 206 of the present embodiment for implementing the present imaging as moving the table stepwise. FIG. 7 (a) and FIG. 7 (b) show examples in which the number of FOV for the imaging is indicated as N. First, the respective steps of FIG. 7 (a) will be described in sequence.

(Step 701)
Setting information relating to the position of N-number of FOV(1)~FOV(N) temporarily stored in the memory of CPU 8 are read out and inputted to sequencer 4.

(Step 702)
Information such as the position of the table is set in the initial position. Further, counter(i) is set at initial value 1.

(Step 703)
The position of the table is moved to the position set in step 204 as to FOV(i). In other words, table 26 is moved along table movement line 302 to longitudinal direction of table 26 (Y-direction in FIG. 4) as well as to the horizontal direction orthogonal to the longitudinal direction of the table (X-direction in FIG. 4), so that the position on the XY-plane in FIG. 4 of the region of the subject corresponding to the central position of the respective FOV(i) being set in step 204 coincides with the position on the XY-plane in the center of static magnetic field of the static magnetic field source of the MRI apparatus. As for the direction to move the table, it may be moved linearly in an oblique direction by synthesizing the components in Y-direction and components in X-direction in FIG. 4, or by dividing the movement into two steps moving the table first to only Y-direction then moving it only to X-direction.

(Step 704)
Information such as imaging condition is set for the purpose of imaging FOV(i). In concrete terms, processing such as setting of spatial resolution inputted in (step 205) and other information to be used for imaging such as applied waveform of gradient magnetic field pulse in the imaging sequence, transmission frequency of RF pulse and reception frequency for detecting echo signals is executed.

(Step 705)
Imaging as to i-th FOV(i) is carried out. Images obtained by the imaging are temporarily stored in magnetic disk 18.

(Step 706)
Whether counter (i) of FOV(i) has reached the maximum value N or not is determined. If reached the imaging is ended, and if not step 707 is to proceed.

(Step 707)
Counter(i) of FOV(i) is incremented and step 703 is to proceed.

Such process is performed in all of FOV(1)~FOV(N).

Next, FIG. 7 (b) is a flow chart showing another example of concrete procedure outline in step 206. Respective steps in FIG. 7 (b) will be described in sequence. FIG. 7 (b) is an example of a case in which table 26 is moved only in longitudinal direction of the table, not in the horizontal direction orthogonal to the longitudinal direction. Also, since FIG. 7 (b) is different from FIG. 7 (a) only in steps 703 and 705, and steps 810 and 711 are provided in place of step 703 and step 712 is provided in place of step 705, description on the common steps will be omitted and only the different steps will be described below.

(Step 710)
Table 26 is moved stepwise only in longitudinal direction of the table. That is, the central position of longitudinal direction of FOV(i) is made to coincide with the central position of longitudinal direction of static magnetic field of the MRI apparatus by moving the table only in longitudinal direction of the table.

(Step 711)
The preparation for carrying out off-center imaging which is for imaging FOV having the position different from the center of static magnetic field as the central position in the horizontal direction orthogonal to the longitudinal direction of the table is executed. More specifically, for example, in the case that one side of the rectangle representing FOV is parallel to longitudinal direction of the table and when a horizontal direction orthogonal to longitudinal direction of the table is set as a frequency encoding direction, a quantity for shifting reception frequency upon quadrature detector 16 detecting echo signals is obtained as a frequency offset value by the following formula (2):

$$\Delta f = -\gamma Gx(\Delta x) \quad (2)$$

In formula (2), $\gamma$ indicates gyromagnetic ratio and Gx indicates the gradient magnetic field output value in frequency encode direction.

Also, in the case that the horizontal direction orthogonal to the longitudinal direction of the table is set as the phasing encode direction, the quantity for shifting the receiver phase upon quadrature detector 16 detecting the echo signals is obtained as an offset value which can be acquired by the following formula:

$$\Delta\theta(e) = -2\pi\{(\Delta y)e\}/My \quad (3)$$

In formula (3), "e" indicates the phasing encode number and "My" indicates the image matrix size in the phasing encode direction. In other words, according to formula (3), the quantity which is proportional to the phasing encode number is set as the phasing offset value for shifting the phase upon detection of the respective echo signals.

Off-center imaging is performed as using the quantity obtained in step 711 as the frequency offset value or phasing offset value. That is to perform off-center imaging corresponding to the case that FOV is off the center of static magnetic field, in the horizontal direction orthogonal to the longitudinal direction of the table.

In the above-mentioned embodiment 1, even when the body axis of a subject is slanted off the initial position of the table movement line (the center axis of longitudinal direction of the table), MRI can be performed by moving the table to a position where the table needs to be for imaging by executing a scanogram in advance to determine the necessary position, or by using methods such as the off-center imaging. In accordance with above-mentioned methods, a problem such as the displacement of the subject in the imaging to be performed while moving the table stepwise can be solved. In embodiment 1, the method for off-center imaging shown in FIG. 7 (*b*) has an advantage that it is capable of performing an effective imaging as the table is moved stepwise corresponding to the displacement of the subject, even when the table can be moved only in longitudinal direction of the table as in the apparatus such as an MRI apparatus of tunnel-type horizontal magnetic field method.

EMBODIMENT 2

Figure 8:
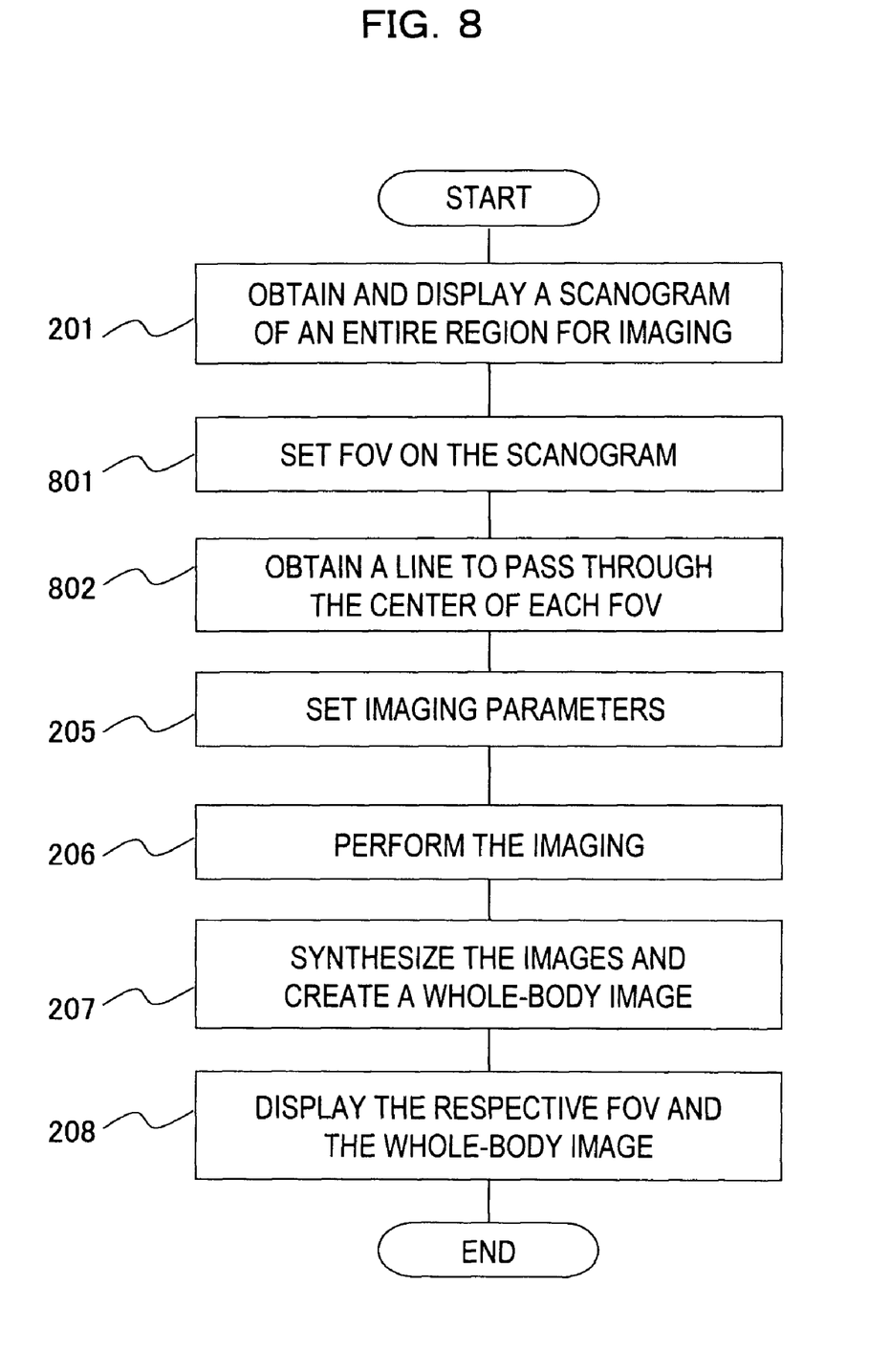
FIG. 8 is a flow chart showing a procedure outline of the MRI in embodiment 2.
Figure 9:
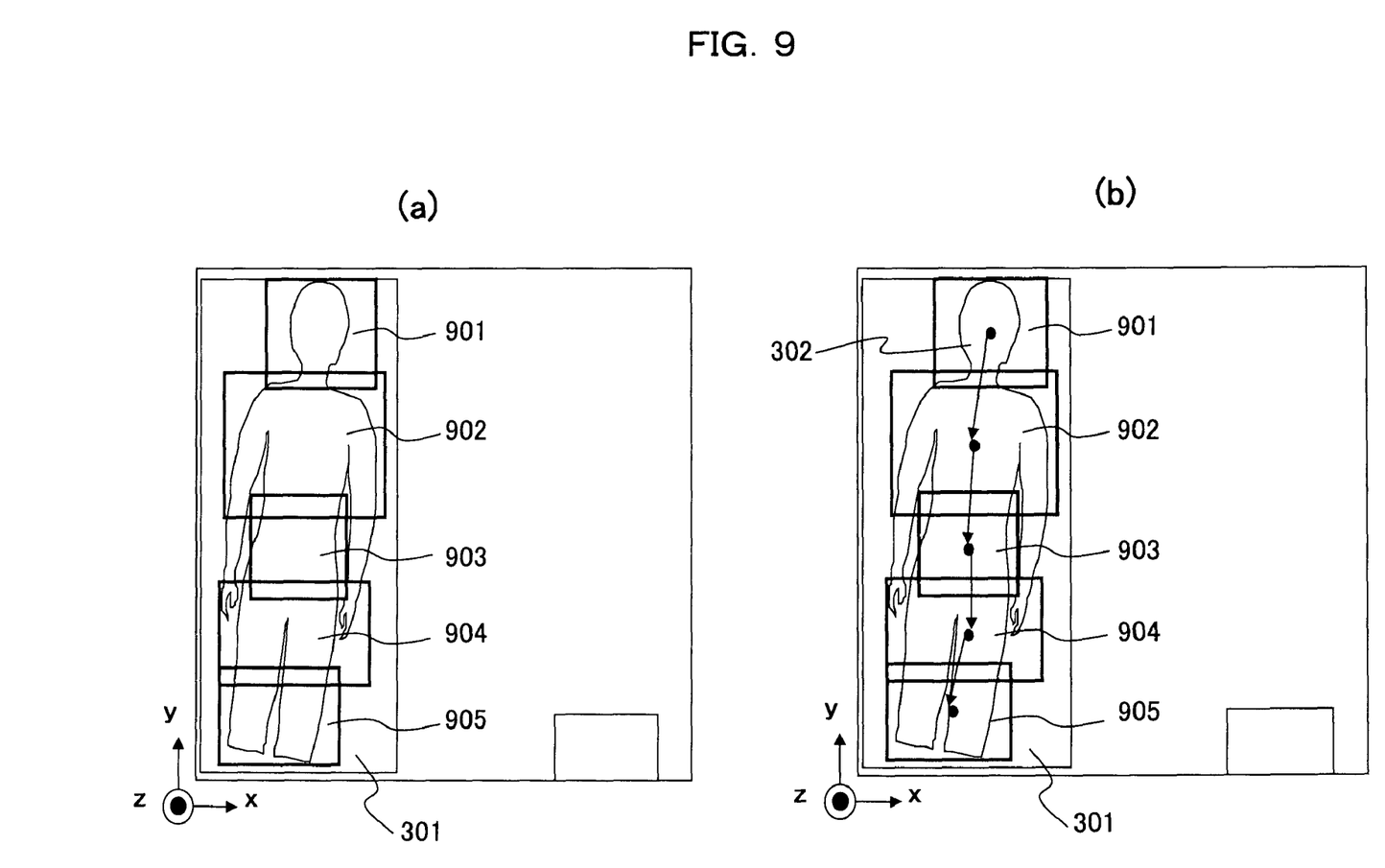
FIG. 9 (a) is a diagram showing a case of setting five FOV 901~905 for imaging coronal sections on scanogram 301, and (b) is a diagram showing an example of acquiring a line to connect the center of FOV 901~905 and set it as table movement line 302.

MRI apparatus and method relating to embodiment 2 of the present invention will be described referring to FIG. 8 and FIG. 9. Embodiment 2 is an apparatus and method, not for setting FOV first so that the center of FOV falls on the central axis of longitudinal direction of the table or on the table movement line as in embodiment 1, but for setting the center of FOV on the unique positions which are not relating to the central axis of longitudinal direction of the table or the table movement line. First, FIG. 8 is a flow chart showing the procedure outline of the MRI in embodiment 2. The respective steps of FIG. 8 will be described in order. Since the only difference that embodiment 2 has compared to FIG. 2 of embodiment 1 is that steps 801 and 802 are provided in place of steps 202~204, thus only steps 801 and 802 that are different from embodiment 1 will be described below.

(Step 801)

A plurality of FOV is set on a scanogram. An example of setting FOV is illustrated in FIG. 9. First, FIG. 9 (*a*) shows a case of setting the rectangles representing five fields of view FOV 901~905 for imaging a coronal section on scanogram 301. As for the setting of FOV 901~905, they are set individually by making the position and size of them correspond to the position and size of the imaging region that each FOV covers. The procedure for adjusting the position and size of the respective FOV is virtually in the same manner as in the case of FIG. 4 (*c*). However, while a case that at least one side of a rectangle representing FOV is parallel to the central axis of longitudinal direction of the table is exemplified in FIG. 9 (*a*), any side may be tilted and not parallel to the central axis of longitudinal direction of the table. In such case, imaging can be performed using the method by oblique imaging as in FIG. 4 (*b*). Information set by the present step will be temporarily stored in, for example, the memory in CPU 8.

(Step 802)

The line to pass through the respective FOV being set in step 801 is obtained, and set as the table movement line. In FIG. 9 (*b*), an example for obtaining the line connecting the center of FOV 901~905 and setting it as table movement line 302 is illustrated. By such setting, in the present imaging of step 206, imaging at the position of FOV being set in step 801 can be implemented by moving the table on the set table movement line.

In the above-mentioned embodiment 2, since imaging of a wide range or the entire body range of a subject can be executed by moving the table effectively through individually setting the respective FOV without setting the imaging line of the subject on a scanogram, it is easier to set the respective FOV by blocks compared to embodiment 1.

EMBODIMENT 3

Figure 10:
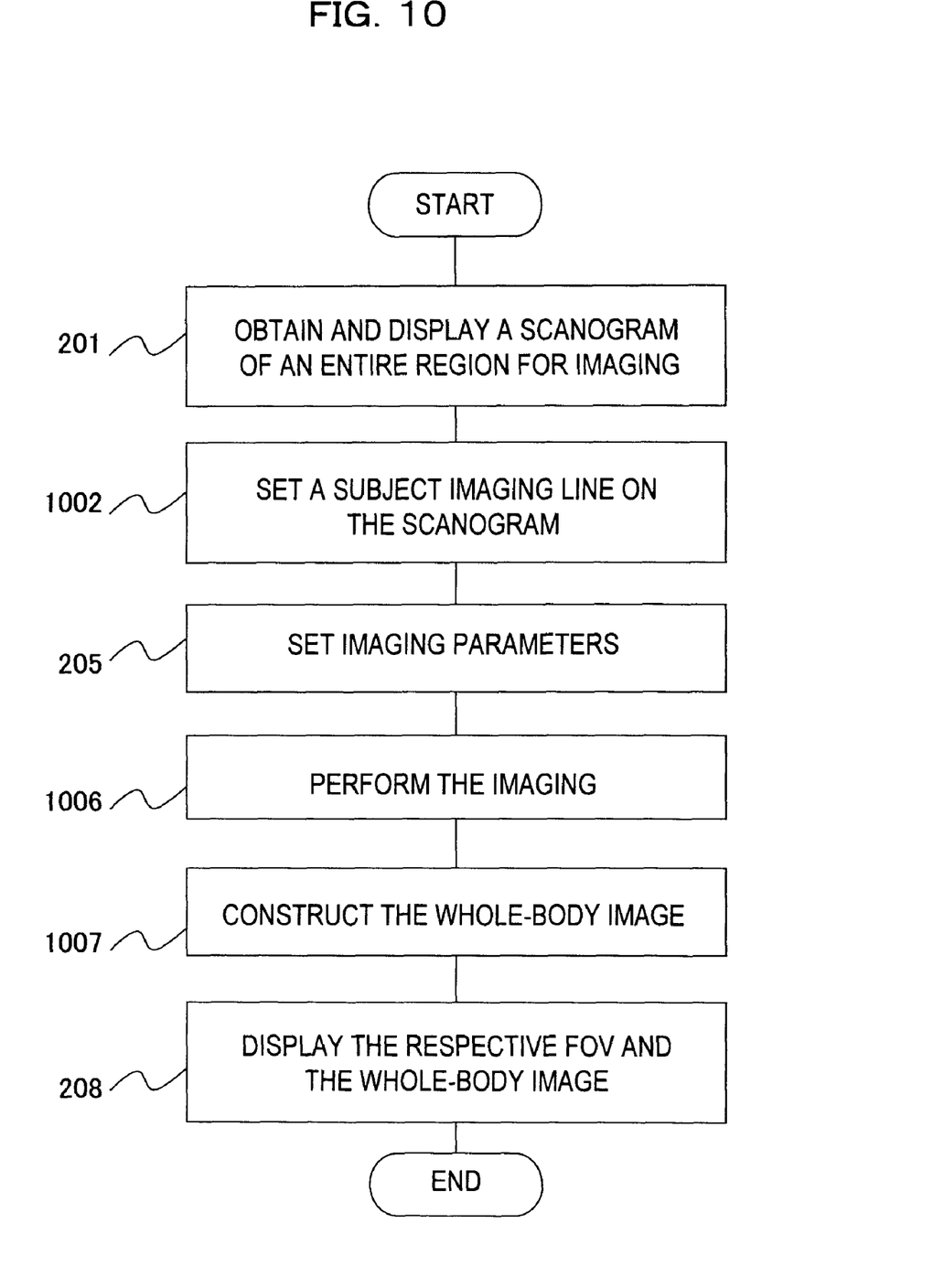
FIG. 10 is a flow chart showing a procedure outline of MRI in embodiment 3.
Figure 11:
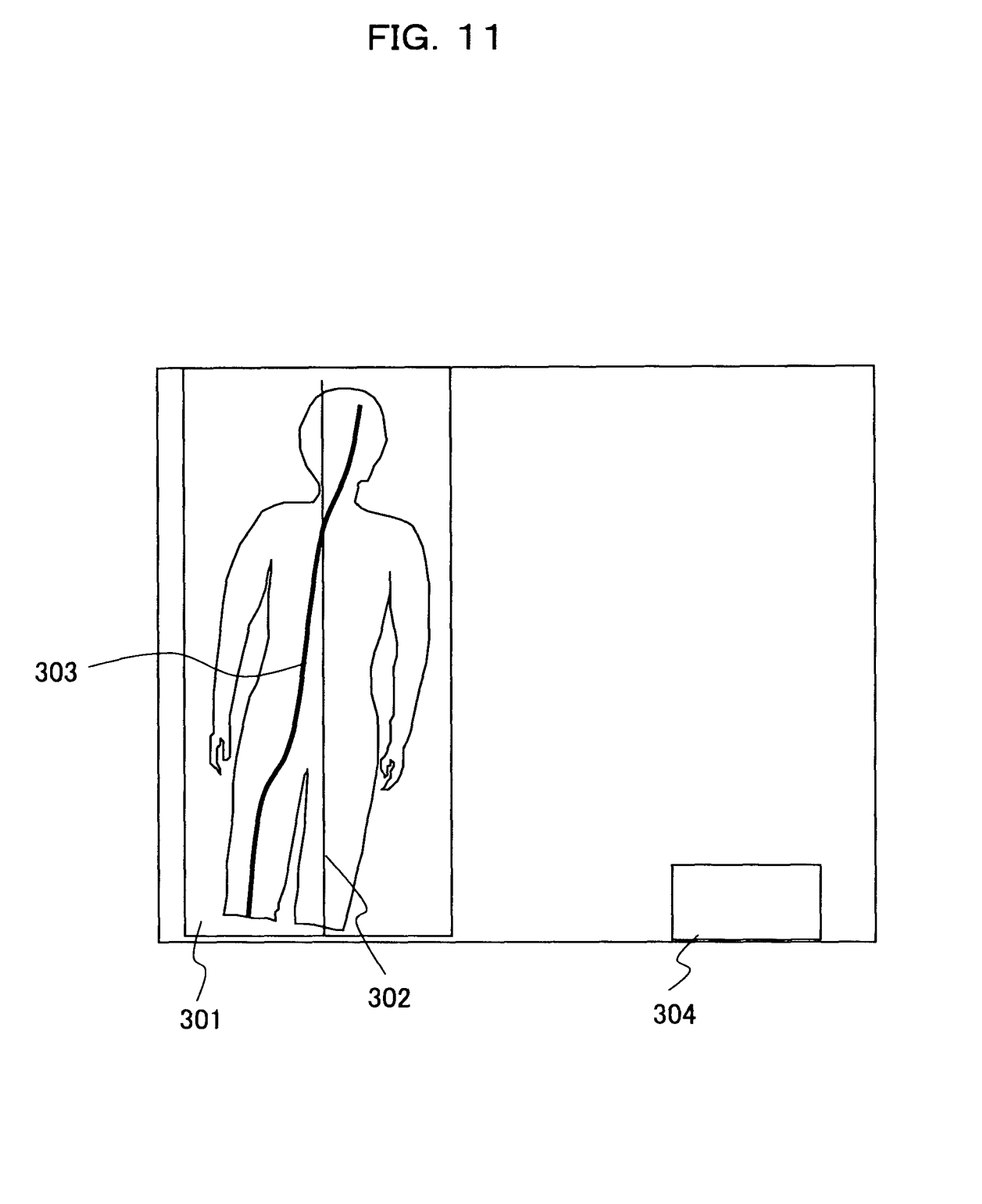
FIG. 11 is a diagram showing an example of drawing a subject imaging line on a scanogram.

An MRI apparatus and method relating to embodiment 3 of the present invention will be described referring to FIG. 10 and FIG. 11. Embodiment 3 is an apparatus and method for continuously imaging a wide range or an entire body range of a subject by continuously moving the table. First, FIG. 10 is a flow chart showing the procedure outline of the MRI in embodiment 3. The respective steps in FIG. 10 will now be described in order. Compared to FIG. 2 in embodiment 1, steps 203 and 204 are eliminated and steps 1002, 1006 and 1007 being slightly different from embodiment 3 are provided in place of steps 202, 206 and 207 in embodiment 3, thus only steps 1002, 1006 and 1007 that are slightly different from embodiment 1 will be described below.

(Step 1002)

The subject imaging line is set on a scanogram. FIG. 11 is an example of plotting the subject imaging line on the scanogram. The example of subject imaging line 303 shown in FIG. 11 is plotted independently of initial position 302 of the table movement line, plotted by trackball or mouse 23, or keyboard 24. The subject imaging line can be a straight line, curved line or combination line of straight and curve lines.

Also, the plotting by trackball or mouse 23, or keyboard 24 can be used for a case of changing the subject imaging line once set.

(Step 1006)

The imaging is performed continuously, as well as direction so that subject imaging line 303 plotted in step 1002 passes through the center of the magnetic field. As a concrete method for imaging in the present step, a method for imaging the cross-sections orthogonal to the central axis of longitudinal direction of the table one slice at a time in the (Step 1007)

Reconstruction of an image is performed on the whole-body image. As for the method for reconstructing the whole-body image, after reconstructing the images being imaged in the respective table positions, the entire imaging can be created by arranging the reconstructed image in the large space including the subject taking into consideration the position in longitudinal direction of the table (Y-direction) upon imaging the respective images and the horizontal direction orthogonal to the Y-direction (X-direction), and by reformatting them in horizontal direction at the cross-section of the predetermined pitch level.

The above-mentioned embodiment 3 has an advantage in the case of continuously imaging a wide range or an entire body range of a subject while continuously moving the table, that the operation for positioning the table can be easily performed by setting only the line for imaging the subject on the image and controlling the table movement so that the set subject imaging line passes through the center of static magnetic field of MRI apparatus.

The present invention is not intended to be limiting to the above-mentioned embodiment, and may be carried out in any suitable fashion within a range that does not deviating from the gist of the present invention. For example, the two-dimensional coronal cross-sections can be imaged in embodiment 1 of the present invention regarding the imaging of the respective FOV, or three-dimensional volume data with thickness in Z-axis direction may be imaged in FIG. 4. Also, the present invention can be applied either to the MRI apparatus of tunnel-type horizontal magnetic field method or to the open MRI apparatus suitable for moving the table two-dimensionally in horizontal direction. Moreover, as for correlating the coordinate system of the static magnetic field of the MRI apparatus with information such as the position where the table is placed, they do not need be correlated on the basis of the origin of the static magnetic field of the MRI apparatus, but may be correlated on the basis of factors such as the position of a corner of the initial position of the table being set in advance or the central position of the first step of FOV for the imaging, to use for a purpose such as calculation of the table movement upon imaging the respective FOV for making the center of the respective FOV the center of static magnetic field. Also, a scanogram does not always have to be used for detecting how much the subject is tilted while being placed on the table. For example, only data projected in one direction of NMR signals may be used, or the subject being placed on the table may be filmed by a camera for detecting the direction of which the subject is placed.

The invention claimed is:

1. A magnetic resonance imaging apparatus comprising:
   an object moving unit on which an object to be examined is placed for moving the object in a static magnetic field space:
   a measurement control unit for imaging a wide range region of the object by moving the object moving unit and acquiring an image of the wide range region;
   a display unit for displaying the image of the wide range region; and
   an input unit for receiving commands from an operator, characterized in further comprising:
   a movement information setting unit for setting movement information for moving the object moving unit based on the command inputted from the input unit,
   wherein the measurement control unit moves the object moving unit continuously or stepwise based on the set movement information.

2. The magnetic resonance imaging apparatus according to claim 1, wherein the movement information includes one or more positions or lines of the object moving unit.

3. The magnetic resonance imaging apparatus according to claim 2, wherein at least a part of one or more positions or lines of the object moving unit includes a position different from the central axis of the object moving unit in the longitudinal direction.

4. The magnetic resonance imaging apparatus according to claim 2, wherein at least a part of one or more positions or lines of the object moving unit includes a position different from the body axis of the object.

5. The magnetic resonance imaging apparatus according to claim 3, wherein the one or more positions of the object moving unit is a central position of one or more FOVs set on image displayed on the display unit.

6. The magnetic resonance imaging apparatus according to claim 3, wherein the line of the object moving unit is a line that connects the central positions of the plurality of FOVs set on image displayed on the display unit.

7. The magnetic resonance imaging apparatus according to claim 5, wherein one side of the rectangle representing at least one of the FOVs has a gradient with respect to the central axis of the object moving unit in the longitudinal directions.

8. The magnetic resonance imaging apparatus according to claim 2, wherein the line of the object moving unit is the line which is drawn on image displayed on the display unit.

9. The magnetic resonance imaging apparatus according to claim 1, wherein at least a part of movement of the object moving unit includes a moving direction different from the longitudinal direction of the object moving unit.

10. The magnetic resonance imaging apparatus according to claim 1, in the case that the plurality of FOVs set via the input unit are sequentially imaged, wherein:
    the movement information setting unit obtains a frequency offset value or a phasing offset value corresponding to the difference between the central position of the FOV and the central position of the magnetic field in the direction vertical to the longitudinal direction of the object moving unit; and
    the measurement control unit controls imaging of the FOV using the frequency offset value or the phasing offset value.

11. A magnetic resonance imaging apparatus comprising:
    an object moving unit on which an object to be examined is placed for moving the object in a static magnetic field space;
    a measurement control unit for imaging a wide range region of the object by moving the object moving unit and acquiring an image of the wide range region;
    a display unit for displaying the image of the wide range region; and
    an input unit for receiving commands from an operator, characterized in further compromising:
    a movement information setting unit for setting movement information for moving the object moving unit based on the plurality of FOVs being set via the input unit;
    wherein the measurement control unit moves the object moving unit continuously or stepwise based on the set movement information.

12. An object moving method of a magnetic resonance imaging apparatus comprising:
    an object moving unit on which an object to be examined is placed for moving the object in a static magnetic field space;
    a measurement control unit for imaging a wide range region of the object by moving the object moving unit and acquiring an image of the wide range region;
    a display means for displaying the image of the wide range region; and
    an input unit for receiving commands from an operator, characterized in having:
    a step for receiving commands from the operator by the input unit;
    a step for setting movement information for moving the object moving unit based on the command inputted from the input unit; and
    a step for moving the object moving unit continuously or stepwise based on the set movement information.

* * * * *